United States Patent [19]

Wagner et al.

[11] Patent Number: 5,859,025
[45] Date of Patent: Jan. 12, 1999

[54] FLUOROALKYL- AND FLUOROALKOXY-SUBSTITUTED HETEROCYCLIC BRADYKININ ANTAGONISTS, PROCESS FOR THEIR PREPARATION, AND THEIR USE

[75] Inventors: Adalbert Wagner, Gersthofen; Holger Heitsch, Mainz-Kastel; Gerhard Nölken, Sulzbach; Klaus Wirth, Kriftel; Bernward Schölkens, Kelkheim, all of Germany

[73] Assignee: Hoechst Aktiengesellschaft, Frankfurt am Main, Germany

[21] Appl. No.: 819,351

[22] Filed: Mar. 18, 1997

[30] Foreign Application Priority Data

Mar. 19, 1996 [DE] Germany ............... 196 10 784.9

[51] Int. Cl.$^6$ ............... A61K 31/47; C07D 215/20; C07D 215/38; C07D 215/14

[52] U.S. Cl. ............... 514/311; 514/312; 514/313; 546/153; 546/155; 546/156; 546/157; 546/159; 546/174; 546/175

[58] Field of Search ............... 514/311, 312, 514/313; 546/153, 155, 156, 157, 159, 174, 175

[56] References Cited

U.S. PATENT DOCUMENTS

| 5,212,182 | 5/1993 | Musser et al. | 514/314 |
| 5,216,165 | 6/1993 | Mobilio et al. | 546/160 |
| 5,438,064 | 8/1995 | Mobilio et al. | 514/313 |

FOREIGN PATENT DOCUMENTS

| 0 622 361 | 11/1994 | European Pat. Off. |
| WO 96/05202 | 2/1996 | WIPO |
| WO 96/13485 | 5/1996 | WIPO |

OTHER PUBLICATIONS

Hoyer et al., ACE inhibitors as a template for the design of bradykinin B$_2$ receptor antagonists, Chemical Abstracts, vol. 123(9): 111822x (1995).
Gennaro, Reminton's Pharmaceutical Sciences, Mack Publ. Co., vol. 17: 1409–1423 (1985).
König et al., Chem. Ber., vol. 103: 788–798 (1970).
König et al., Chem. Ber., vol. 103: 2052–2061 (1970).
Eichler et al., Handbook of Experimental Pharmacology, Springer Verlag, vol. 25 (S): 53–55 (1979).
Wirth et al., Hoe 140 a new potent and long acting bradykinin–antagonist: in vivo studies, Br. J. Pharmacol., vol. 102: 774–777 (1991).
Innis et al., [$^3$H]Bradykinin receptor binding in mammalian tissue membranes, Proc. Natl. Acad. Sci, USA, vol. 78 (4): 2630–2634 (1981).
EPO Search Report of EPO Application No. 97103611.6 dated Jul. 1, 1997.

*Primary Examiner*—Mukund J. Shah
*Assistant Examiner*—Brenda Coleman
*Attorney, Agent, or Firm*—Finnegan, Henderson, Farabow, Garrett & Dunner, L.L.P.

[57] ABSTRACT

Fluoroalkyl- and fluoroalkoxy-substituted heterocyclic bradykinin antagonists, process or their preparation, and their use Heterocyclic fluoroalkyl derivatives and fluoroalkoxy derivatives of the formula (I) having bradykinin-antagonistic action

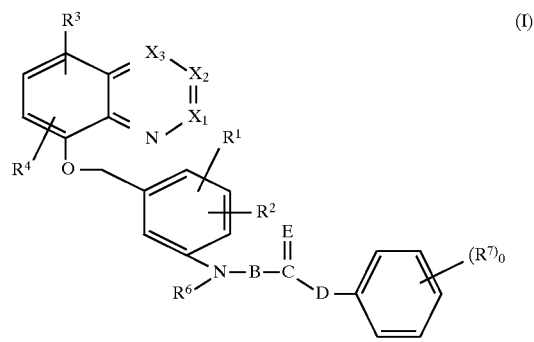

in which $X_1$–$X_3$ are N or $CR^5$, $R^1$ and $R^2$ are H or halogen, $R^3$ and $R^4$ are H, halogen, alkyl or alkenyl, $R^5$ is H, halogen, (substituted) alkyl, O—$R^6$, S—$R^6$, $NHR^6$, (substituted) aryl, (substituted)aryl-alkyl, —C(O)—$OR^6$ or —C(O)—H, $R^6$ and $R^8$ H, alkyl, alkenyl or aryl-alkyl, $R^7$ is (substituted) alkyl or (substituted) alkoxy, B is an aminocarboxylic acid, D is alkenediyl, alkanediyl or —$(CH_2)_n$—$Y_p$—$(CH_2)_m$—, E is oxygen or sulfur, Y is oxygen, sulfur or $NR^8$, n and m are a number 0–3, o is a number 1–3 and p is 0 or 1, and their physiologically tolerable salts and a process for their preparation are described.

35 Claims, No Drawings

FLUOROALKYL- AND FLUOROALKOXY-SUBSTITUTED HETEROCYCLIC BRADYKININ ANTAGONISTS, PROCESS FOR THEIR PREPARATION, AND THEIR USE

The invention relates to heterocyclic fluoroalkyl-substituted and fluoroalkoxy-substituted compounds having bradykinin-antagonist action.

EP-A 622 361, U.S. Pat. Nos. 5,212,182, 5,216,165 and 5,438,064 disclose O- and N-substituted quinolines and their use as bradykinin receptor antagonists.

It has surprisingly been found that the introduction of fluoroalkyl groups yields compounds which have a distinctly longer duration of action.

The present invention relates to heterocyclic fluoroalkyl derivatives and fluoroalkoxy derivatives of the formula (I)

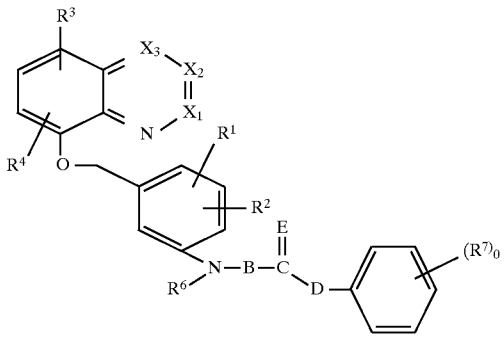

in which the symbols have the following meaning:
a) $X_1$–$X_3$, identically or differently, are N or $CR^5$;
b) $R^1$ and $R^2$, identically or differently, are
  (1) H
  (2) halogen;
c) $R^3$ and $R^4$, identically or differently, are
  (1) H
  (2) halogen
  (3) $(C_1–C_5)$-alkyl
  (4) $(C_2–C_5)$-alkenyl;
d) $R^5$ is
  (1) H
  (2) halogen
  (3) $(C_1–C_6)$-alkyl
  (4) O—$R^6$
  (5) S—$R^6$
  (6) $NHR^6$
  (7) $(C_6–C_{12})$-aryl
  (8) $(C_6–C_{12})$-aryl-$(C_1–C_3)$-alkyl
  (9) —C(O)—$OR^6$
  (10) —C(O)—H;
where (3), (7) and (8) can optionally be substituted by one or more groups such as, for example, $OR^6$, $SR^6$, $NO_2$, CN, $NHR^6$ or halogen
e) $R^6$ and $R^8$, identically or differently, are
  (1) H
  (2) $(C_1–C_5)$-alkyl
  (3) $(C_3–C_5)$-alkenyl
  (4) $(C_6–C_{12})$-aryl-$(C_1–C_3)$-alkyl;
f) $R^7$ is
  (1) $(C_1–C_5)$-alkyl, where hydrogen is partially or completely replaced by fluorine or chlorine
  (2) $(C_1–C_5)$-alkoxy, where hydrogen is partially or completely replaced by fluorine or chlorine;
g) B is an aminocarboxylic acid, e.g. methionine, alanine, phenylalanine, 2-chlorophenylalanine, 3-chlorophenylalanine, 4-chlorophenylalanine, 2-fluorophenylalanine, 3-fluorophenylalanine, 4-fluorophenylalanine, tyrosine, O-methyltyrosine, β-(2-thienyl)alanine, glycine, cyclohexylalanine, leucine, isoleucine, valine, norleucine or phenylglycine, serine or cysteine, aminopropionic acid, aminobutyric acid;
h) D is
  (1) $(C_2–C_5)$-alkenediyl
  (2) $(C_1–C_5)$-alkanediyl
  (3) —$(CH_2)_n$—$Y_p$—$(CH_2)_m$—;
i) E is
  (1) O
  (2) S;
j) Y is
  (1) O
  (2) S
  (3) $NR^8$;
k) n and m, identically or differently, are a number 0–3;
l) o is a number 1–3;
m) p is a number 0 or 1;
and their physiologically tolerable salts.

Alkyl and alkenyl can be straight-chain or branched. The same applies to radicals derived therefrom such as, for example, alkoxy.

$(C_6–C_{12})$-aryl is, for example, phenyl, naphthyl or biphenyl, preferably phenyl. The same also applies to radicals derived therefrom, such as, for example, aralkyl.

Halogen (Hal) is fluorine, chlorine, bromine or iodine, preferably chlorine.

Physiologically tolerable salts of compounds of the formula (I) are understood as meaning both their organic and inorganic salts, as are described in Remington's Pharmaceutical Sciences (A. R. Gennard (Editor), Mack Publishing Co., Easton, Pa., 17th edition, pages 1418 (1985)). On account of the physical and chemical stability and the solubility, for acidic groups, inter alia, sodium, potassium, calcium and ammonium salts are preferred; for basic groups, inter alia, salts of hydrochloric acid, sulfuric acid, phosphoric acid or of carboxylic acids or sulfonic acids, such as, for example, acetic acid, citric acid, benzoic acid, maleic acid, fumaric acid, tartaric acid and p-toluenesulfonic acid are preferred.

Preferred compounds of the formula (I) are those in which
a) $X_1$–$X_3$ are $CR^5$;
b) $R^3$ and $R^4$, identically or differently, are
  (1) H
  (2) $(C_1–C_3)$-alkyl
  (3) $(C_3–C_5)$-alkenyl;
c) $R^5$ is
  (1) H
  (2) $(C_1–C_6)$-alkyl
  (3) O—$R^6$
  (4) S—$R^6$
  (5) $NHR^6$
  (6) $(C_6–C_{12})$-aryl
  (7) $(C_6–C_{12})$-aryl-$(C_1–C_3)$-alkyl
  (8) —C(O)—$OR^6$
  (9) —C(O)—H
in which $R^6$ is as defined in formula (I) above.

Particularly preferred compounds of the formula (I) are those in which a) B is leucine, isoleucine, valine, alanine, methionine, glycine, serine, aminopropionic acid, aminobutyric acid;
b) $R^7$ is
(1) $CF_3$
(2) $OCF_3$;
c) o is 1–2.

The invention furthermore relates to a process for the preparation of compounds of the formula (I), which comprises a) deprotonating a compound of the formula (II),

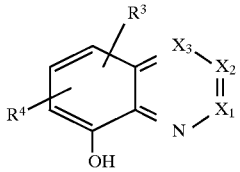

in which $X_1$–$X_3$ and $R^3$ and $R^4$ are as defined in formula (I) above, using $Cs_2CO_3$ or $K_2CO_3$ in an inert solvent, preferably DMF or N-methylpyrrolidine, and reacting it at room temperature with a compound of the formula (III)

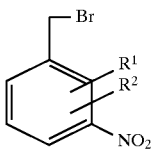

in which $R^1$ and $R^2$ are as defined in formula (I) above;

b) reducing the compound thus obtained of the formula (IV)

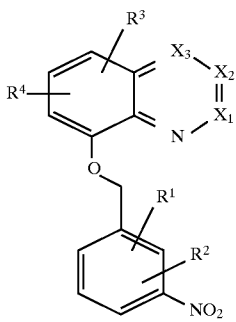

in which $R^1$, $R^2$, $R^3$, $R^4$, $X_1$, $X_2$ and $X_3$ are as defined in formula (I) above, with the aid of transition metal halides, preferably $SnCl_2$ or $FeCl_3$, to give a compound of the formula (V)

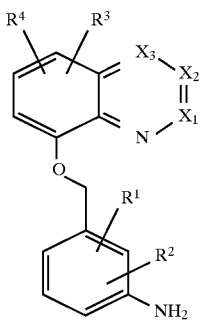

in which $R^1$, $R^2$, $R^3$, $R^4$, $X_1$, $X_2$ and $X_3$ are as defined in formula (I) above;

c) reacting a compound of the formula (V) with activated, suitably protected aminocarboxylic acid derivatives of B (B-Prot), preferably the acid chlorides of the phthaloyl-protected aminocarboxylic acid derivatives of B, in inert solvents such as, for example, NMP, if appropriate by addition of DMAP, and thus obtaining a compound of the formula (VI)

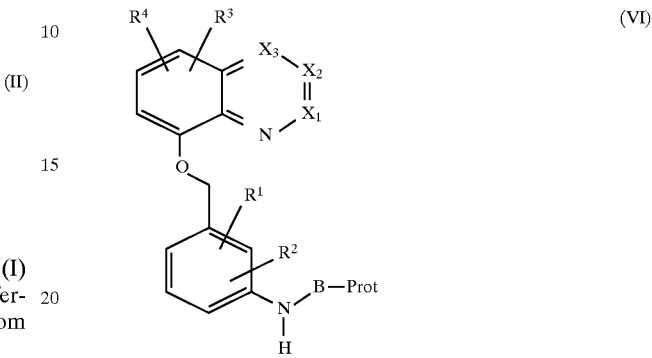

in which B, $R^1$, $R^2$, $R^3$, $R^4$, $X_1$, $X_2$ and $X_3$ are as defined in formula (I) above, and Prot is an amino protective group, such as described in T. W. Greene "Protective Groups in organic Synthesis", John Wiley, 2nd Edition, 1991, e.g. phthaloyl, benzyl or paramethoxybenzyl;

d) reacting a compound of the formula (VI), after action of alkali metal hydrides, alkali metal carbonates or alkoxides in inert solvents, preferably DMF or NMP, has taken place, followed by a treatment with $R^6X$, where $R^6$ is as defined in formula (I) above and X is a leaving group, e.g. halogen, mesylate or tosylate, a compound of the formula (VII) being obtained

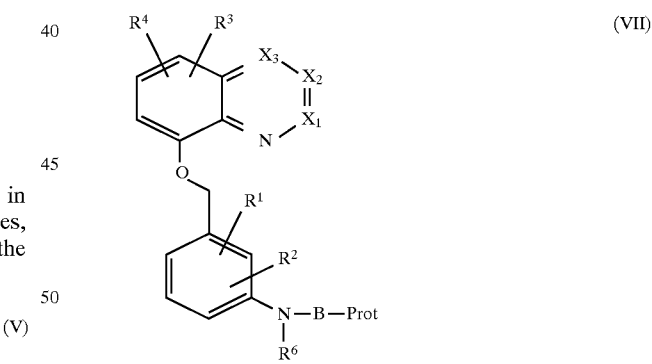

in which B, $R^1$, $R^2$, $R^3$, $R^4$, $R^6$, $X_1$, $X_2$ and $X_3$ are as defined in formula (I) above and Prot is as defined in formula (VI) above;

e) to remove the protective group (Prot) from the compound of the formula (VII), in the case of the phthaloyl group preferably reacting with hydrazine in alcohols as solvents at temperatures between room temperature and the boiling point, preferably at room temperature, a compound of the formula (VIII) being obtained

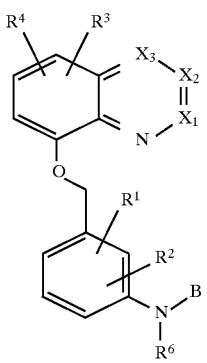

in which B, $R^1$, $R^2$, $R^3$, $R^4$, $R^6$, $X_1$, $X_2$ and $X_3$ are as defined in formula (I) above and Prot is as defined in formula (VI) above;

$f_1$) reacting a compound of the formula (VIII) with activated carboxylic acid derivatives of the formula (IX)

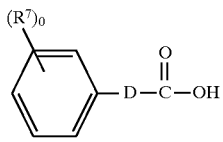

in which $R^7$, o and D are as defined in formula (I) above, preferably their acid chlorides or carboxylic acids of the formula (IX), activated by reagents such as are used in peptide synthesis, or $f_2$) reacting a compound of the formula (VIII) with an amine or an alcohol of the formula (X)

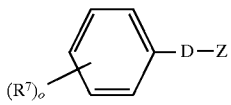

in which $R^7$, o and D are as defined above and Z is OH or $NH_2$, the compound of the formula (VIII) or (X), however, first being reacted with a doubly activated carbonyl compound to form the urea or urethane group, e.g. with carbodiimides, phosgene or chlorocarbonic acid esters, preferably phosgene and carbonyidiimidazole, preferably at temperatures between 0° C. and room temperature in inert solvents, preferably dichloromethane or dimethoxyethane, or $f_3$) reacting a compound of the formula (VIII) with an appropriate isocyanate or isothiocyanate, preferably at temperatures between 0° C. and room temperature in inert solvents, preferably dichloromethane or dimethoxyethane, and g) if appropriate, converting the compound of the formula (I) obtained into its physiologically tolerable salts by known methods.

Conversion to the bromomethyl compound is carried out by reaction of the corresponding methyl derivative with N-bromosuccinimide, dibromohydantoin or bromine in inert solvents, preferably bromobenzene or cyclohexane at temperatures from 60° C. up to the boiling point.

The coupling reagent used can be all possible activating reagents used in peptide synthesis, see, for example, Houben-Weyl, Methoden der Organischen Chemie, [Methods of Organic Chemistry], volume 15/2, Georg Thieme Verlag, Stuttgart 1974, but in particular carbodiimides such as, for example, N,N'-dicyclohexylcarbodiimide, N,N'-diisopropyl-carbodiimide or N-ethyl-N'-(3-dimethylaminopropyl)carbodiimide. Coupling can be carried out in this case directly by addition of carboxylic acid derivative to the activating reagent and, if appropriate, an additive such as, for example, 1-hydroxybenzotriazole (HOBt) (W. König, R. Geiger, Chem. Ber. 103, 708 (1970)) or 3-hydroxy-4-oxo-3,4-dihydrobenzotriazine (HOObt) (W. König, R. Geiger, Chem. Ber. 103, 2054 (1970)) or else the preactivation of the carboxylic acid derivative as a symmetrical anhydride or HOBt or HOObt ester can be carried out separately and the solution of the activated species in a suitable solvent can be added to the amine.

The coupling or activation of the amino acid derivatives to one of the abovementioned activating reagents can be carried out in dimethylformamide, N-methylpyrrolidone or methylenechloride or a mixture of the solvents mentioned.

Instead of the phthaloyl group, protective groups can also be used which protect both protons of the amino group, e.g. 2 benzyl groups.

The compounds according to the invention, individually or in combination, have a bradykinin antagonistic action which can be tested in various models (see Handbook of Exp. Pharmacol. Vol. 25, Springer Verlag, 1970, pp. 53–55), for instance on the isolated rat uterus, on the guinea-pig ileum, the jugular vein of the rabbit or on the isolated pulmonary artery of the guinea-pig. The effects of the compounds of the formula (I) on bradykinin induced bronchoconstriction and carrageenin-induced paw edema can be determined analogously to Br. J. Pharmacol. 102, 774–777 (1991).

The measurement of the binding to the bradykinin $B_2$ receptor of the guinea-pig ileum is described in the following (R. B. Innis et al., Proc. Natl. Acad. Sci. USA; 17 (1981) 2630):

1. Ligand
   $^3$H-BRADYKININ (from NEN Du Pont)
2. Buffer Mixtures
   a) TES-buffer:
      25 mM TES (SIGMA, Order No: T-4152)
      1 mM 1,10-phenanthroline (SIGMA; Order No: P-9375)
   b) Incubation buffer:
      25 mM TES (SIGMA; Order No.: T-4152)
      1 mM 1,10-phenanthroline (SIGMA; Order No.: P-9375)
      0,1% albumin, bovine (SIGMA; Order No.: A-7906)
      140 mg/ml bacitracin (SIGMA; Order No.: B-0125)
      1 mM dithiothreitol (SIGMA; Order No.: D-0632)
      1 mM captopril® 1-[(2S)-3-mercapto-2-methylpropionyl]-L-proline
   Both buffers are adjusted to pH 6.8 using 5 molar NaOH.
3. Membrane Preparation
   The guinea-pig ilea are roughly freed of the intestinal contents by careful stripping and cleaned in 0.9% strength NaCl solution. The pieces of ilea, which are about 2 cm long, are transferred to ice-cold TES buffer (about 1 g/10 ml) and homogenized in an ice-bath for 30 sec. using an Ultraturrax. The homogenate is then filtered through 3 layers of gauze and the filtrate is centrifuged at 50,000 g for 10 minutes. The supernatant is discarded, and the pellet is rehomogenized in the same volume of TES buffer and centrifuged again at 50,000 g for 10 minutes. The pellet is rehomogenized in incubation buffer (about 1 g/5 ml) and frozen at −70° C. in cryotubes, divided into 2 ml portions.
   The protein concentration of the ready-to-use membrane suspension is determined according to LOWRY and should be about 15 mg/100 ml.
4. Binding Test
   All incubations are carried out at room temperature for 60 minutes on microtiter plates (96×300 ml) in 200 ml volumes.

All mixtures in incubation buffer. To this end, 50 ml of the radioligand, 50 ml of the preparation to be tested and 100 ml of the membrane suspension are pipetted successively into the depressions of the microtiter plate.

a) Saturation Experiments (hot saturation)

Preparation of the $^3$H-bradykinin solution: For the saturation experiments, the concentrations 0.05, 0.1, 0.2, 0.4, 0.6, 0.8, 1.0, 1.5, 2.0, 2.5 and 3.0 nmol/l are employed, which correspond to 0.05 to 3.0 pmol/ml. After the preparation of the corresponding dilutions, 50 ml each per sample are initially introduced.

Nonspecific binding: For each concentration of the radioactive ligand, the nonspecific binding must be determined. This can be achieved by addition of a high concentration (1–100 mmol) of the unlabeled ligand, other antagonists or agonists of the bradykinin receptor. In this test, HOE 140 (J. Knolle et al., Recent Progress on Kinins, *New and Highly Potent Bradykinin Antagonists*, p. 559–564, Birkhäuser Verlag, Basel (1992)) (10 mmol/l) is used. For this, 1.862 mg are dissolved in 1 ml of dimethyl sulfoxide (DMSO), diluted 1:25 with incubation buffer and 50 ml of this solution are added to the samples in the microtiter plates. The reaction is started by the addition of 100 ml of the membrane suspension.

b) Competition Experiments (IC$_{50}$)

Here a fixed quantity of the radioactive ligand (0.25 to 0.3 nmol/l of $^3$H-bradykinin) and various concentrations of the unlabeled agonists or antagonists are employed. 50 ml of the preparations or standards to be tested in the concentrations $10^{-5}$ to $10^{-10}$ mol/l are added to in each case 50 ml of the $^3$H-bradykinin solution and the reaction is started by addition of 100 ml of membrane suspension. In this test too, triplicate determinations are carried out and three samples are incubated with 10 mmol/l of HOE 140 to determine the nonspecific binding.

The preparations to be tested for competition are always dissolved at a concentration of 1 mmol/l in dimethyl sulfoxide (DMSO), and then further diluted with DMSO. This solution is then diluted 1:25 with incubation buffer.

After incubation, the samples are filtered off in a Skatron cell harvester through a Whatmann GF/B filter previously moistened with 0.1% PEI (polyethylenimine) and washed with 10 ml of ice-cold TES buffer per sample. The still moist filters are punched out into mini-scintillation tubes and the tubes are filled with 3 ml of scintillator. After about 12 hours soaking time, the samples are briefly shaken and measured in a beta counter.

c) Screening

In primary screening, in general only 1–2 concentrations of the test preparation ($10^{-5}$ and $10^{-6}$ mol/l) are employed. If at the highest concentration a displacement of the radioligand of 50% or more is detectable, a complete analysis (competition experiment) is carried out using at least 8 concentrations.

4. Assessment

The assessment is carried out by means of the LIGAND program package (Mc Pherson, Minson & Rodbard, Marketing organization: Elsevier-BIOSOFT), which performs the necessary calculations to determine IC$_{50}$ and K$_i$ values. This program additionally carries out graphical presentations of the saturation and displacement curves and also the SCATCHARD plot, HILL plot or HOFSTEE plot.

5. Test Results

The following IC$_{50}$ and K$_i$ values were determined by the abovementioned process for the compounds of Examples 1, 2, 8, 22 and 29 as representative compounds of the described fluoroalkyl- and fluoroalkoxy-substituted heterocyclic bradykinin antagonists of the formula (I):

| Example | IC$_{50}$ [nM] | K$_i$ [nM] |
| --- | --- | --- |
| 1 | 9.0 | 1.0 |
| 2 | 40.0 | 4.0 |
| 8 | 28.0 | 3.4 |
| 22 | 95.0 | 10.0 |
| 29 | 38.0 | 5.1 |

The determinations of the antagonist action on the bradykinin-induced contraction of the guinea-pig ileum were carried out according to the following protocol:

Guinea-pigs weighing about 300 g (Morioth strain,__) are killed by a blow to the neck and exsanguinated. The ileum is dissected out in a length of about 20 cm, rinsed with Tyrode solution (Record syringe) and thus freed of intestinal contents. It is then divided into sections 1.5 cm long. These are fixed in organ baths of capacity 10 ml, which are filled with Tyrode solution, and connected to extension-measuring strips (isometric contraction measurement). The preload is 1 g. The Tyrode solution is warmed to 37° C. in a water bath and bubbled through with compressed air. After an interval of 30 min. the experiment is begun. After recording the biological zero line, bradykinin at a final concentration of $4 \times 10^{-8}$ mol/l per organ bath is added and the concentration is recorded. The organ bath is then rinsed for 3 min with Tyrode solution and, after a break of 20 min., bradykinin is added again. The maximum of the contraction is achieved (control). Rinse again, break. The bradykinin antagonist is then added (time of action 10 min). Bradykinin is then added again and the ensuing contraction is compared with that of the control. The experiment is recorded on a pen recorder.

Tyrode Solution (mM)

| NaCl | 137 |
| --- | --- |
| Glucose | 5.05 |
| KCl | 2.68 |
| NaHCO$_3$ | 11.9 |
| NaH$_2$PO$_4$ | 0.47 |
| MgCl$_2$ × 2H$_2$O | 0.49 |
| CaCl$_2$ × 2H$_2$O | 0.68 |

Amplifier: TF6 V3 Fleck, Mainz

Pen recorder: Goerz Metrawatt SE 460, BBC

Bradykinin: Bachem

Thus the compounds of Examples 1 and 2, for example, have the following IC$_{50}$ values determined according to the above process:

| Example | IC$_{50}$ [nM] |
| --- | --- |
| 1 | 44.0 |
| 2 | 1500.0 |

The distinctly prolonged duration of action of the compounds of the formula (I) was detected in the jugular vein of the rabbit and is described below:

The compounds of Examples 1, X and Y were compared. Examples X and Y are described in EP-A 622 361.

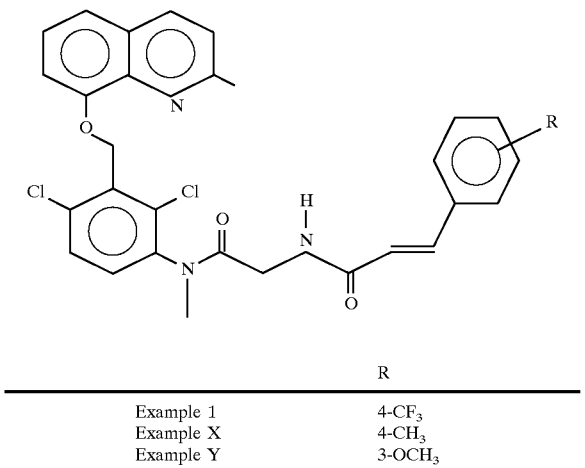

| | R |
|---|---|
| Example 1 | 4-CF$_3$ |
| Example X | 4-CH$_3$ |
| Example Y | 3-OCH$_3$ |

Comparison of the in-vitro duration of action of heterocyclic bradykinin antagonists on the isolated rabbit jugular

| | Inhibition of the bradykinin contraction in % | | |
|---|---|---|---|
| time (min) | Ex. Y ($10^{-5}$) | Ex. 1 ($10^{-5}$) | Ex. X ($10^{-5}$) |
| 15' | 96 | 98 | 97 |
| 30' | 97 | 99 | 97 |
| 60' | 96 | 99 | — |
| 120' | — | — | 95 |
| 150' | — | — | 87 |
| 180' | 84 | 98 | 74 |
| 210' | 59 | 95 | 58 |
| 240' | 31 | 92 | 30 |
| 270' | 3 | 87 | — |
| 300' | — | 78 | — |
| 330' | — | 71 | — |
| 360' | — | 68 | — |

Method Description

Male rabbits (white New Zealand, breeder: Möllegaard, Denmark, 2.5–3.0 kg) are killed by injection of an overdose of Pentobarbital-Na (1 ml of Narcoren®+0.5 ml of heparin). The two jugular veins are exposed, cut spirally and pieces of about 1.5 cm length are suspended in buffered organ baths (Krebs-Henseleit buffer) at a pretension of 0.5 g.

After a rest period of 30 min, contractions are induced by addition of bradykinin ($10^{-7}$M), which serve as the starting value. Test substances are then added at a concentration of $10^{-5}$M. The inhibitory values shown are mean values (n=6). The values indicated at time 15 min show the inhibition of the bradykinin-induced contraction additionally in the presence of the test substances in the bath fluid after incubation for 15 minutes. The bradykinin contraction is then ended by rinsing with just buffer solution.

At each further time shown, stimulation was again carried out with bradykinin (in the absence of the test substance in the bath fluid) and at the end of the contraction the bath fluid was replaced by just buffer solution.

Results

In comparison to the compounds of Examples Y and X, the compound of Example 1 shows superiority in the form of a distinctly longer in-vitro duration of action. This is a measure of the strength of the binding to the receptor. The compounds of Examples Y and X no longer show any inhibition after 4 h, while the compound of Example 1 still exhibits 68% inhibitory action after 6 h.

For the oral administration form or for application to the mucous membrane, the active compounds are mixed with the additives customary for this such as excipients, stabilizers or inert diluents and brought by customary methods into suitable administration forms, such as tablets, coated tablets, hard gelatin capsules, aqueous, alcoholic or oily suspensions or aqueous, alcoholic or oily solutions. Inert excipients which can be used are, for example, gum arabic, magnesia, magnesium carbonate, potassium phosphate, lactose, glucose, magnesium stearyl fumarate or starch, in particular corn starch. In this case, preparation can take place both as dry and moist granules. Suitable oily excipients or solvents are, for example, vegetable or animal oils, such as sunflower oil and fish liver oil.

A preparation for topical application can be present as an aqueous or oily solution, lotion, emulsion or gel, ointment or fatty ointment or, if possible, in spray form, it optionally being possible to improve the adhesion by addition of a polymer.

For the intranasal administration form, the compounds are mixed with the customary additives for this such as stabilizers or inert diluents and brought by customary methods into suitable administration forms, such as aqueous, alcoholic or oily suspensions or aqueous, alcoholic or oily solutions. Chelating agents, ethylenediamine-N,N,N',N'-tetraacetic acid, citric acid, tartaric acid or their salts can be added to aqueous intranasal preparations. The nasal solutions can be administered by means of metered atomizers or as nasal drops having a viscosity-enhancing component or nasal gels or nasal creams.

The compounds of the formula (I) described and their pharmacologically suitable salts are potent bradykinin antagonists. Their therapeutic use therefore lies in the treatment and/or the prevention of all pathological conditions which are mediated, induced or assisted by bradykinin and bradykinin-analogous peptides. This includes, inter alia, allergies, inflammations, autoimmune disorders, shock, pain and, more especially, asthma, cough, bronchitis, rhinitis, chronic obstructive pulmonary disorders, pneumonitis, septic shock, endotoxic shock, anaphylactic shock, disseminating intravascular coagulopathy, arthritis, rheumatism, osteoarthritis, lumbago, inflammation-induced bone resorption, conjunctivitis, iritis, headache, migraine, toothache, back pain, cancer-related pain, post-operative pain, traumata (wounds, burns etc.), exanthema, erythema, edema, eczema, dermatitis, shingles, herpes, pruritus, psoriasis, lichen, inflammatory intestinal disorders, hepatitis, pancreatitis, gastritis, esophagitis, food allergies, ulcers, irritable bowel, angina, cerebral edema, low blood pressure, thrombosis, craniocerebral and spinal trauma, premature delivery, atherosclerosis, ascites in cancer, tumor metastases, cerebral edema in tumors, heat damage to the brain and viral disorders.

As it is furthermore known that bradykinin is linked to the release of mediators such as prostaglandins, leukotrienes, tachykinins, histamine and thromboxanes, the compounds of the formula (I) thus also have potential for the treatment and/or prevention of the diseases which are caused by these mediators.

The invention therefore also relates to the use of compounds of the formula (I) as therapeutics and to pharmaceutical preparations which contain these compounds.

Pharmaceutical preparations contain an effective amount of the active compound of the formula (I)—individually or in combination—together with an inorganic or organic pharmaceutically utilizable excipient.

Administration can be carried out enterally, parenterally—such as, for example, subcutaneously, i.m. or i.v., sublingually, epicutaneously, nasally, rectally, intravaginally, intrabuccally or by inhalation. The dose of the active compound depends on the warm-blooded species, the body weight, age and on the type of administration.

The pharmaceutical preparations of the present invention are prepared in dissolving, mixing, granulating or sugar-coating processes which are known per se.

For administration by inhalation, atomizers or pressurized gas packs using inert carrier gases can be used.

For intravenous, subcutaneous, epicutaneous or intradermal administration, the active compounds or their physiologically tolerable salts are brought into solution, suspension or emulsion, if desired with the pharmaceutically customary auxiliaries, for example for isotonisization or pH adjustment, and solubilizers, emulsifiers or other auxiliaries.

Should the half-lives of the pharmaceutical substances described in body fluids be inadequate, the use of injectable delayed-release preparations is useful. Pharmaceutical forms which can be used are, for example, oily crystal suspensions, microcapsules, rods or implants, it being possible to construct the latter from tissue-tolerable polymers, in particular biodegradeable polymers, such as, for example, on the basis of polylactic acid—polyglycolic acid copolymers or human albumin.

A suitable dose range for forms to be administered topically and by inhalation are solutions containing 0.01–5 mg/l; in the case of systemic administration forms 0.01–10 mg/kg are suitable. Generally, amounts between 0.1 mg up to 1000 mg can be administered to an adult (75 kg bodyweight) per day.

List of Abbreviations

| | |
|---|---|
| AIBN | a,a'-Azobisisobutyronitrile |
| DEI | Desorption electron impact |
| DCI | Desorption-chemical ionization |
| EA | Ethyl acetate |
| FAB | Fast atom bombardment |
| DME | Dimethoxyethane |
| DMF | Dimethylformamide |
| DMAP | Dimethylaminopyridine |
| NMP | N-Methylpyrrolidone |
| n-H | n-Heptane |
| RT | Room temperature |
| $CH_2Cl_2$ | Dichloromethane |
| h | hours |
| ESI | Electron spray ionization |

The invention is illustrated by the examples below.

EXAMPLE 1

8-[3-(N-(4-trans-Trifluoromethylcinnamoylglycyl)-N-methylamino)-2,6-dichlorobenzyloxy]-2-methylquinoline a) 2,6-Dichloro-3-nitrobenzyl Bromide A mixture of dibromohydantoin (70 g, 0.24 mol) and AIBN (5 g) was added in portions at 150° C. to 2,6-dichloro-3-nitrotoluene (100 g, 0.48 mol) in chlorobenzene (400 ml). After 1 h, a mixture of dibromohydantoin (35 g, 0.12 mol) and AIBN (2.5 g) was again added. After a further 1.5 h, the mixture was allowed to cool and EA (500 ml) was added. This mixture was washed once each with saturated $Na_2SO_3$, $Na_2CO_3$ and NaCl solution, dried ($MgSO_4$) and concentrated, the title compound being obtained as an amorphous powder.

$R_f$(EA/nH 1/1)=0.7 MS (DEI)=283 ($M^+$)

b) 8-(2,6-Dichloro-3-nitrobenzyloxy)-2-methylquinoline $Cs_2CO_3$ (10.8 g, 33.3 mmol) was added at room temperature to 8-hydroxy-2-methylquinoline (5 g, 33.3 mmol) in DMF (65 ml). After 30 min, 2,6-dichloro-3-nitrobenzyl bromide (13 g, 45.6 mmol) was added. After 18 h, $H_2O$ was added and the precipitate was filtered off with suction and washed with EA (50 ml), the title compound being obtained as an amorphous substance.

$R_f$(EA/n-H 1/2)=0.3 MS (DEI)=362 (M)

c) 8-(2,6-Dichloro-3-aminobenzyloxy)-2-methylquinoline $SnCl_2H_2O$ (15 g, 66.6 mmol) was added to the title compound of Example 1 b) (4.5 g, 12.4 mmol) in EA (60 ml) and the suspension was heated to 70° C. After 1 h, the mixture was concentrated in vacuo after cooling to room temperature and 20% NaOH solution (100 ml) was added and the mixture was then extracted three times with $CH_2Cl_2$. The combined organic phases were dried over $CaCl_2$ and concentrated.

$R_f$(EA/n-H 1/1)=0.4 MS (FAB)=333 (M+1)

d) 8-(2,6-Dichloro-3-phthaloylglycylaminobenzyloxy)-2-methylquinoline

Phthaloylglycyl chloride (3.4 g, 15 mmol) was added to the title compound of Example 1 c) (3.2 g, 10 mmol) and DMAP (1.2 g, 10 mmol) in NMP (30 ml) and pyridine (10 ml). The mixture was heated at 50° C. for 1.5 h, cooled to 0° C. and $H_2O$ (30 ml) was added. The precipitate was filtered off with suction and washed with EA (100 ml), the title compound being obtained as an amorphous powder.

$R_f$(EA/n-H 1/1)=0.2 MS (FAB)=520 (M+1)

e) 8-[3-(N-Phthaloylglycyl-N-methylamino)-2,6-dichlorobenzyloxy]-2-methylquinoline Sodium hydride (313 mg of a 60% suspension; ~8 mmol) was added at 0° C. to the title compound of Example 1 d) (3.7 g, 7.1 mmol) in DMF (40 ml). After 30 min, methyl iodide (0.5 ml, 0.8 mmol) was injected. The cooling was then removed and after 1 h the mixture was again cooled to 0° C. and $H_2O$ (75 ml) was added. The title compound was filtered off with suction and washed with cold $CH_3OH$ (30 ml).

$R_f$(EA/n-H 1/1)=0.2 MS (FAB)=534 (M+1)

f) 8-[3-(N-Glycyl-N-methylamino)-2,6-dichlorobenzyloxy]-2-methylquinoline

The title compound of Example 1 e) (1.5 g, 2.8 mmol) and hydrazine hydrate 0.54 ml, 11.2 mmol) in ethanol (60 ml) were stirred at room temperature for 12 h. The mixture was then concentrated and $CH_2Cl_2$ (40 ml) was added and the mixture was filtered and the solid residue was washed with $CH_2Cl_2$ (40 ml). Concentration of the $CH_2Cl_2$ solution yielded the title compound as a pale yellow foam.

$R_f$(EA/$CH_3OH$ 1/1)=0.25 MS (FAB)=404 (M+1)

g) Trans-4-Trifluoromethylcinnamoyl Chloride

Thionyl chloride (335 ml, 4.6 mmol) was added at 0° C. to 4-trifluoromethyl-E-cinnamic acid (1 g, 4.6 mmol) and pyridine (375 ml, 4.6 mmol) in dry $CH_2Cl_2$. The mixture was then stirred for 1 h without cooling, again cooled to 0° C. and filtered with the exclusion of moisture. The filtrate (10 ml) contained the title compound and was used in aliquots for the next reaction step.

h) 8-[3-(N-(4-trans-Trifluoromethylcinnamoylglycyl)-N-methylamino)-2,6-dichlorobenzyloxy]-2-methylquinoline An aliquot of the solution of the title compound of Example 1 g) (2 ml, 1.5 eq, 0.9 mmol) was added at room temperature to the title compound of Example 1 f) (250 mg, 0.6 mmol) in $CH_2Cl_2$ (3 ml). After 18 h, saturated $Na_2CO_3$ solution (10 ml) was added and the mixture was extracted 3 times with $CH_2Cl_2$ (3×20 ml). The organic phases were dried ($CaCl_2$) and concentrated. Chromatography on $SiO_2$ using EA as the eluent yielded the title compound of Example 1 as an amorphous powder.

$R_f$(EA)=0.4 MS (ESI)=602 (M+1)

The compounds of Examples 2 to 6, 8, 9, 12, and 13 were obtained analogously to Example 1 and compounds of Examples 7, 10, and 11 can be obtained analogously to Example 1 (Tables 1 and 2).

TABLE 1

| Example | R | MS (M + H) | $R_f$ (EA) |
|---|---|---|---|
| 2 | 5-methylquinolin-8-yl | 616 | 0.3 |
| 3 | 6-methylquinolin-8-yl | 616 | 0.3 |
| 4 | 7-propyl-2-methylquinolin-8-yl | 644 | 0.4 |
| 6 | 2,5-dimethylquinolin-8-yl | 630 | 0.5 |

TABLE 2

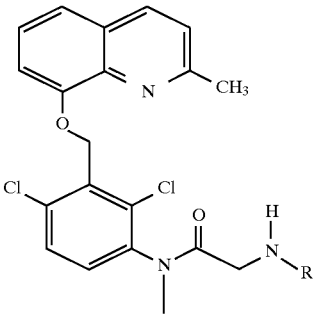

| Example | R | MS (M + H) |
|---|---|---|
| 6 | 2-(trifluoromethyl)phenylacetaldehyde-derived | 590 |
| 7 | 3-(trifluoromethyl)phenylacetaldehyde-derived | |
| 8 | 4-(trifluoromethyl)phenylacetaldehyde-derived | 590 |
| 9 | 2-(trifluoromethyl)benzaldehyde-derived | 576 |
| 10 | 3-(trifluoromethyl)benzaldehyde-derived | |
| 11 | 4-(trifluoromethyl)benzaldehyde-derived | |
| 12 | 3-(trifluoromethyl)cinnamaldehyde-derived | 602 |
| 13 | 2-(trifluoromethyl)cinnamaldehyde-derived | 602 |

EXAMPLE 14

8-[2,6-Dichloro-3-(N-(4-trifluoromethylbenzyloxycarbonylaminoacetyl)-N-methylamino)benzyloxy]-2-methylquinoline 4-Trifluoromethylbenzyl alcohol (65 mg, 0.37 mmol), 1,1-carbonyldiimidazole (60 mg, 0.37 mmol) and DMAP (10 mg) were stirred at room temperature for 6 h in dichloromethane (5 ml). The title compound of Example 1 f) (150 mg, 0.37 mmol) was then added and after a further 18 h ethyl acetate (40 ml) was added. The mixture was washed once each with saturated $Na_2CO_3$ and NaCl solution, dried using $MgSO_4$ and concentrated. The title compound was obtained as a colorless foam.

$R_f$(EA)=0.5 MS (FAB)=606 (M+1)

The compounds of Examples 15 to 18, 20, and 22 were obtained analogously to Example 14 and compounds of Examples 17, 21, 23, and 24 can be obtained analogously to Example 14 (Table 3).

TABLE 3

| Example | R | MS (M + 1) |
|---|---|---|
| 15 | 2-CF3-benzyl-O- | 606 |
| 16 | 3-CF3-benzyl-O- | 606 |
| 17 | 2-CF3-phenethyl-O- | 620 |
| 18 | 3-CF3-phenethyl-O- | 620 |
| 19 | 2-CF3-α-methylbenzyl-O- | |
| 20 | 3-CF3-α-methylbenzyl-O- | 620 |
| 21 | 4-CF3-α-methylbenzyl-O- | |
| 22 | 4-CF3O-benzyl-O- | 622 |
| 23 | 4-CF3O-phenyl-O- | |
| 24 | 3-OCF3-phenyl-O- | |

EXAMPLE 25

8-[3-(N-(4-Trifluoromethylphenylureidoacetyl)-N-methylamino)-2,6-dichlorobenzyloxy]-2-methylquinoline 4-Trifluoromethylphenyl isocyanate (93 mg, 0.49 mmol) was added to the title compound of Example 1 f) (200 mg, 0.49 mmol) in DME (10 ml). After 3 h at room temperature, the solvent was removed in vacuo. Chromatography on $SiO_2$ with EA as eluent yielded the title compound.

$R_f$(EA)=0.4 MS (ESI)=591 (M+1)

The compound of Example 27 was obtained analogously to Example 25 and compounds of Examples 26 and 28 can be obtained analogously to Example 25 (Table 4).

TABLE 4

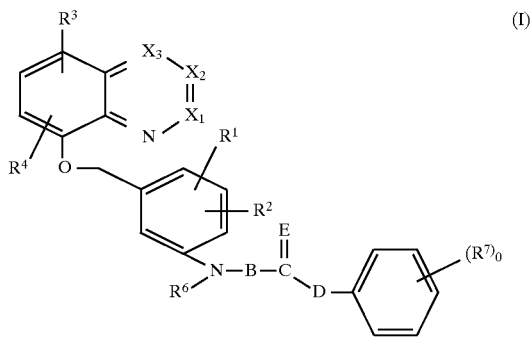

| Example | R | MS (M + 1) |
|---|---|---|
| 26 | (3-CF₃-phenyl)-NH- | |
| 27 | (2-OCF₃-phenyl)-NH- | 610 |
| 28 | (4-F₃CO-phenyl)-NH- | |

EXAMPLE 29

8-[3-N-(3-Trifluoromethylphenylthioureidoacetyl-N-methylamino)-2,6-dichlorobenzyloxy]-2-methylquinoline 3-Trifluoromethylphenyl isothiocyanate (50 mg, 0.24 mmol) was added at room temperature to the title compound of Example 1 f) (100 mg, 0.24 mmol) in DME (4 ml). After 2 hours, the mixture was concentrated in vacuo and chromatographed on $SiO_2$ using EA as eluent, the title compound being obtained.

$R_f$(EA)=0.5 MS (FAB)=607 (M+1)

What is claimed is:

1. A heterocyclic fluoroalkyl compound or fluoroalkoxy compound of the formula (I)

in which the symbols have the following meaning:
a) $X_1$–$X_3$ are $CR^5$;
b) $R^1$ and $R^2$, identically or differently, are
  (1) H
  (2) halogen;
c) $R^3$ and $R^4$, identically or differently, are
  (1) H
  (2) halogen
  (3) ($C_1$–$C_5$)-alkyl
  (4) ($C_2$–$C_5$)-alkenyl;
d) $R^5$ is
  (1) H
  (2) halogen
  (3) ($C_1$–$C_6$)-alkyl
  (4) O—$R^6$
  (5) S—$R^6$
  (6) NH$R^6$
  (7) ($C_6$–$C_{12}$)-aryl
  (8) ($C_6$–$C_{12}$)-aryl-($C_1$–$C_3$)-alkyl
  (9) —C(O)—O$R^6$
  (10) —C(O)—H;
where (3), (7), and (8) can optionally be substituted by one or more groups O$R^6$, S$R^6$, $NO_2$, CN, NH$R^6$ or halogen;
e) $R^6$ and $R^8$, identically or differently, are
  (1) H
  (2) ($C_1$–$C_5$)-alkyl
  (3) ($C_3$–$C_5$)-alkenyl
  (4) ($C_6$–$C_{12}$)-aryl-($C_1$–$C_3$)-alkyl;
f) $R^7$ is
  (1) ($C_1$–$C_5$)-alkyl, where hydrogen is partially or completely replaced by fluorine or chlorine
  (2) ($C_1$–$C_5$)-alkoxy, where hydrogen is partially or completely replaced by fluorine or chlorine;
g) B is an aminocarboxylic acid;
h) D is
  (1) ($C_2$–$C_5$)-alkenediyl
  (2) ($C_1$–$C_5$)-alkanediyl
  (3) —($CH_2$)$_n$—$Y_p$—($CH_2$)$_m$—;
i) E is
  (1) O
  (2) S;
j) Y is
  (1) O
  (2) S
  (3) N$R^8$;
k) n and m, identically or differently, are a number from 0 to 3;
l) o is a number from 1 to 3;
m) p is 0 or 1;
a physiologically tolerated salt thereof.

2. A heterocyclic fluoroalkyl compound or fluoroalkoxy compound of the formula (I) as claimed in claim 1, in which
a) $X_1$–$X_3$ are $CR^5$;
b) $R^3$ and $R^4$, identically or differently, are
  (1) H
  (2) ($C_1$–$C_3$)-alkyl
  (3) ($C_3$–$C_5$)-alkenyl;
c) $R^5$ is
  (1) H
  (2) ($C_1$–$C_6$)-alkyl
  (3) O—$R^6$
  (4) S—$R^6$
  (5) NH$R^6$
  (6) ($C_6$–$C_{12}$)-aryl
  (7) ($C_6$–$C_{12}$)-aryl-($C_1$–$C_3$)-alkyl (8) —C(O)—OR⁶
(9) —C(O)—H
in which R⁶ is as defined in claim 1 or a physiologically tolerated salt thereof.

3. A heterocyclic fluoroalkyl compound or fluoroalkoxy compound of the formula (I) as claimed in claim 1 in which
a) B is leucine, isoleucine, valine, alanine, methionine, glycine, serine, aminopropionic acid, or aminobutyric acid;
b) R⁷ is
(1) CF₃
(2) OCF₃;
c) o is 1 or 2; or a physiologically tolerated salt thereof.

4. A heterocyclic fluoroalkyl compound or fluoroalkoxy compound of the formula (I) as claimed in claim 2 in which
a) B is leucine, isoleucine, valine, alanine, methionine, glycine, serine, aminopropionic acid, or aminobutyric acid;
b) R⁷ is
(1) CF₃
(2) OCF₃;
c) o is 1 or 2; or a physiologically tolerated salt thereof.

5. A heterocyclic fluoroalkyl compound or fluoroalkoxy compound of the formula (I) as claimed in claim 1, which is 8-[3-(N-(4-trans-Trifluoromethylcinnamoylglycyl)-N-methylamino)-2,6-dichlorobenzyloxy]-2-methylquinoline, or a physiologically tolerated salt thereof.

6. A heterocyclic fluoroalkyl compound or fluoroalkoxy compound of the formula (I) as claimed in claim 1, which is 8-[3-(N-(4-trans-Trifluoromethylcinnamoylglycyl)-N-methylamino)-2,6-dichlorobenzyloxy]-2,5-dimethylquinoline, or a physiologically tolerated salt thereof.

7. A heterocyclic fluoroalkyl compound or fluoroalkoxy compound of the formula (I) as claimed in claim 1, which is 8-[3-(N-(4-trans-Trifluoromethylcinnamoylglycyl)-N-methylamino)-2,6-dichlorobenzyloxy]-2,6-dimethylquinoline, or a physiologically tolerated salt thereof.

8. A heterocyclic fluoroalkyl compound or fluoroalkoxy compound of the formula (I) as claimed in claim 1, which is 8-[3-(N-(4-trans-Trifluoromethylcinnamoylglycyl)-N-methylamino)-2,6-dichlorobenzyloxy]-2-methyl-7-propylquinoline, or a physiologically tolerated salt thereof.

9. A heterocyclic fluoroalkyl compound or fluoroalkoxy compound of the formula (I) as claimed in claim 1, which is 8-[3-(N-(4-trans-Trifluoromethylcinnamoylglycyl)-N-methylamino-2,6-dichlorobenzyloxy]-2,5,7-trimethylquinoline, or a physiologically tolerated salt thereof.

10. A heterocyclic fluoroalkyl compound or fluoroalkoxy compound of the formula (I) as claimed in claim 1, which is 8-[3-(N-((2-Trifluoromethylphenylacetyl)glycyl)-N-methylamino)-2,6-dichlorobenzyloxy]-2-methylquinoline, or a physiologically tolerated salt thereof.

11. A heterocyclic fluoroalkyl compound or fluoroalkoxy compound of the formula (I) as claimed in claim 1, which is 8-[3-(N-((3-Trifluoromethylphenylacetyl)glycyl)-N-methylamino)-2,6-dichlorobenzyloxy]-2-methylquinoline, or a physiologically tolerated salt thereof.

12. A heterocyclic fluoroalkyl compound or fluoroalkoxy compound of the formula (I) as claimed in claim 1, which is 8-[3-(N-((4-Trifluoromethylphenylacetyl)glycyl)-N-methylamino)-2,6-dichlorobenzyloxy]-2-methylquinoline, or a physiologically tolerated salt thereof.

13. A heterocyclic fluoroalkyl compound or fluoroalkoxy compound of the formula (I) as claimed in claim 1, which is 8-[3-(N-(2-Trifluoromethybenzoylglycyl)-N-methylamino)-2,6-dichlorobenzyloxy]-2-methylquinoline, or a physiologically tolerated salt thereof.

14. A heterocyclic fluoroalkyl compound or fluoroalkoxy compound of the formula (I) as claimed in claim 1, which is 8-[3-(N-(3-Trifluoromethylbenzoylglycyl)-N-methylamino)-2,6-dichlorobenzyloxy]-2-methylquinoline, or a physiologically tolerated salt thereof.

15. A heterocyclic fluoroalkyl compound or fluoroalkoxy compound of the formula (I) as claimed in claim 1, which is 8-[3-(N-(4-Trifluoromethylbenzoylglycyl)-N-methylamino)-2,6-dichlorobenzyloxy]-2-methylquinoline, or a physiologically tolerated salt thereof.

16. A heterocyclic fluoroalkyl compound or fluoroalkoxy compound of the formula (I) as claimed in claim 1, which is 8-[3-(N-(3-trans-Trifluoromethylcinnamoylglycyl)-N-methylamino)-2,6-dichlorobenzyloxy]-2-methylquinoline, or a physiologically tolerated salt thereof.

17. A heterocyclic fluoroalkyl compound or fluoroalkoxy compound of the formula (I) as claimed in claim 1, which is 8-[3-(N-(2-trans-Trifluoromethylcinnamoylglycyl)-N-methylamino)-2,6-dichlorobenzyloxy]-2-methylquinoline, or a physiologically tolerated salt thereof.

18. A heterocyclic fluoroalkyl compound or fluoroalkoxy compound of the formula (I) as claimed in claim 1, which is 8-[2,6-Dichloro-3-(N-(4-trifluoromethylbenzyloxycarbonylaminoacetyl)-N-methylamino)benzyloxy]-2-methylquinoline, or a physiologically tolerated salt thereof.

19. A heterocyclic fluoroalkyl compound or fluoroalkoxy compound of the formula (I) as claimed in claim 1, which is 8-[2,6-Dichloro-3-(N-(2-trifluoromethylbenzyloxycarbonylaminoacetyl)-N-methylamino)benzyloxy]-2-methylquinoline, or a physiologically tolerated salt thereof.

20. A heterocyclic fluoroalkyl compound or fluoroalkoxy compound of the formula (I) as claimed in claim 1, which is 8-[2,6-Dichloro-3-(N-(3-trifluoromethylbenzyloxycarbonylaminoacetyl)-N-methylamino)benzyloxy]-2-methylquinoline, or a physiologically tolerated salt thereof.

21. A heterocyclic fluoroalkyl compound or fluoroalkoxy compound of the formula (I) as claimed in claim 1, which is 8-[2,6-Dichloro-3-(N-(2-(2-trifluoromethylphenyl)ethoxycarbonylaminoacetyl)-N-methylamino)benzyloxy]-2-methylquinoline, or a physiologically tolerated salt thereof.

22. A heterocyclic fluoroalkyl compound or fluoroalkoxy compound of the formula (I) as claimed in claim 1, which is 8-[2,6-Dichloro-3-(N-(2-(3-trifluoromethylphenyl)ethoxycarbonylaminoacetyl)-N-methylamino)benzyloxy]-2-methylquinoline, or a physiologically tolerated salt thereof.

23. A heterocyclic fluoroalkyl compound or fluoroalkoxy compound of the formula (I) as claimed in claim 1, which is 8-[2,6-Dichloro-3-(N-(2-trifluoromethyl-a-methylbenzyloxycarbonylaminoacetyl)-N-methylamino)benzyloxy]-2-methylquinoline, or a physiologically tolerated salt thereof.

24. A heterocyclic fluoroalkyl compound or fluoroalkoxy compound of the formula (I) as claimed in claim 1, which is 8-[2,6-Dichloro-3-(N-(3-trifluoromethyl-a-methylbenzyloxycarbonylaminoacetyl)-N-methylamino)benzyloxy]-2-methylquinoline, or a physiologically tolerated salt thereof.

25. A heterocyclic fluoroalkyl compound or fluoroalkoxy compound of the formula (I) as claimed in claim 1, which is 8-[2,6-Dichloro-3-(N-(4-trifluoromethyl-a-methylbenzyloxycarbonylaminoacetyl)-N-methylamino)benzyloxy]-2-methylquinoline, or a physiologically tolerated salt thereof.

26. A heterocyclic fluoroalkyl compound or fluoroalkoxy compound of the formula (I) as claimed in claim 1, which is 8-[2,6-Dichloro-3-(N-(4-trifluoromethoxybenzyloxycarbonylaminoacetyl)-N-methylamino)benzyloxy]-2-methylquinoline, or a physiologically tolerated salt thereof.

27. A heterocyclic fluoroalkyl compound or fluoroalkoxy compound of the formula (I) as claimed in claim 1, which is 8-[2,6-Dichloro-3-(N-(4-trifluoromethoxyphenoxycarbonylaminoacetyl)-N-methylamino)benzyloxy]-2-methylquinoline, or a physiologically tolerated salt thereof.

28. A heterocyclic fluoroalkyl compound or fluoroalkoxy compound of the formula (I) as claimed in claim 1, which is 8-[2,6-Dichloro-3-(N-(3-trifluoromethoxyphenoxycarbonylaminoacetyl)-N-methylamino)benzyloxy]-2-methylquinoline, or a physiologically tolerated salt thereof.

29. A heterocyclic fluoroalkyl compound or fluoroalkoxy compound of the formula (I) as claimed in claim 1, which is 8-[3-(N-(4-Trifluoromethylphenylureidoacetyl)-N-methylamino)-2,6-dichlorobenzyloxy]-2-methylquinoline, or a physiologically tolerated salt thereof.

30. A heterocyclic fluoroalkyl compound or fluoroalkoxy compound of the formula (I) as claimed in claim 1, which is 8-[3-(N-(3-Trifluoromethylphenylureidoacetyl)-N-methylamino)-2,6-dichlorobenzyloxy]-2-methylquinoline, or a physiologically tolerated salt thereof.

31. A heterocyclic fluoroalkyl compound or fluoroalkoxy compound of the formula (I) as claimed in claim 1, which is 8-[3-(N-(2-Trifluoromethoxyphenylureidoacetyl)-N-methylamino)-2,6-dichlorobenzyloxy]-2-methylquinoline, or a physiologically tolerated salt thereof.

32. A heterocyclic fluoroalkyl compound or fluoroalkoxy compound of the formula (I) as claimed in claim 1, which is 8-[3-(N-(4-Trifluoromethoxyphenylureidoacetyl)-N-methylamino)-2,6-dichlorobenzyloxy]-2-methylquinoline, or a physiologically tolerated salt thereof.

33. A heterocyclic fluoroalkyl compound or fluoroalkoxy compound of the formula (I) as claimed in claim 1, which is 8-[3-N-(3-Trifluoromethylphenylthioureidoacetyl-N-methylamino)-2,6-dichlorobenzyloxy]-2-methylquinoline, or a physiologically tolerated salt thereof.

34. A pharmaceutical composition comprising a heterocyclic fluoroalkyl derivative or fluoroalkoxy compound of the formula (I) as claimed in claim 1; or a physiologically tolerated salt thereof.

35. A method of treating pain comprising administering an effective amount of a heterocyclic fluoroalkyl derivative or fluoroalkoxy derivative of the formula (I) as claimed in claim 1; or a physiologically tolerated salt thereof.

* * * * *

UNITED STATES PATENT AND TRADEMARK OFFICE
CERTIFICATE OF CORRECTION

PATENT NO.    : 5,859,025
DATED         : January 12, 1999
INVENTOR(S)   : Adalbert Wagner et al.

It is certified that error appears in the above-identified patent and that said Letters Patent is hereby corrected as shown below:

Column 18,
Line 50, after "1;" insert -- or --.

Column 19,
Line 3, after "claim 1" insert -- ; --.

Column 20,
Line 58, "benzyioxy" should read -- benzyloxy --.

Column 22,
Lines 21 and 25, "fluroalkyl derivative" should read -- fluroalkyl compound --.
Line 26, "fluroalkoxy derivative" should read -- fluroalkyloxy compound --.

Signed and Sealed this

Eighteenth Day of June, 2002

Attest:

JAMES E. ROGAN
Attesting Officer    Director of the United States Patent and Trademark Office